United States Patent
Ruddick

(10) Patent No.: US 6,172,221 B1
(45) Date of Patent: Jan. 9, 2001

(54) CLAVULANIC ACID EXTRACTION PROCESS

(75) Inventor: Simon Ruddick, Worthing (GB)

(73) Assignee: SmithKline Beecham p.l.c., Brentford (GB)

(*) Notice: Under 35 U.S.C. 154(b), the term of this patent shall be extended for 0 days.

(21) Appl. No.: 08/875,240

(22) PCT Filed: Jan. 17, 1996

(86) PCT No.: PCT/EP96/00270

§ 371 Date: Aug. 27, 1997

§ 102(e) Date: Aug. 27, 1997

(87) PCT Pub. No.: WO96/22296

PCT Pub. Date: Jul. 25, 1996

(30) Foreign Application Priority Data

Jan. 19, 1995 (GB) .................................................. 9500977

(51) Int. Cl.[7] ..................... C07D 501/12; C07D 499/04; C07D 487/08

(52) U.S. Cl. ........................... 540/220; 540/346; 540/349

(58) Field of Search .............................. 424/114; 514/200, 514/196; 435/119; 540/220, 346, 349

(56) References Cited

U.S. PATENT DOCUMENTS 4,110,165 * 8/1978 Cole et al. ........................... 424/114

FOREIGN PATENT DOCUMENTS

| 0 026 044 | 4/1981 | (EP) . |
| 0 153 843 | 9/1985 | (EP) . |
| 95 21173 | 8/1995 | (WO) . |
| 95 23870 | 9/1995 | (WO) . |

* cited by examiner

Primary Examiner—John Kight
Assistant Examiner—Raymond Covington
(74) Attorney, Agent, or Firm—Zoltan Kerekes; Stephen Venetianer; Charles M. Kinzig

(57) ABSTRACT

A back extraction process in which beta-lactam antibiotics or clavulanic acid is extracted from an organic solvent phase into an aqeous medium phase, using a mixing region in which the phases are mixed rapidly under high turbulence and shear stress.

27 Claims, 2 Drawing Sheets

CLAVULANIC ACID EXTRACTION PROCESS

Figure 1:
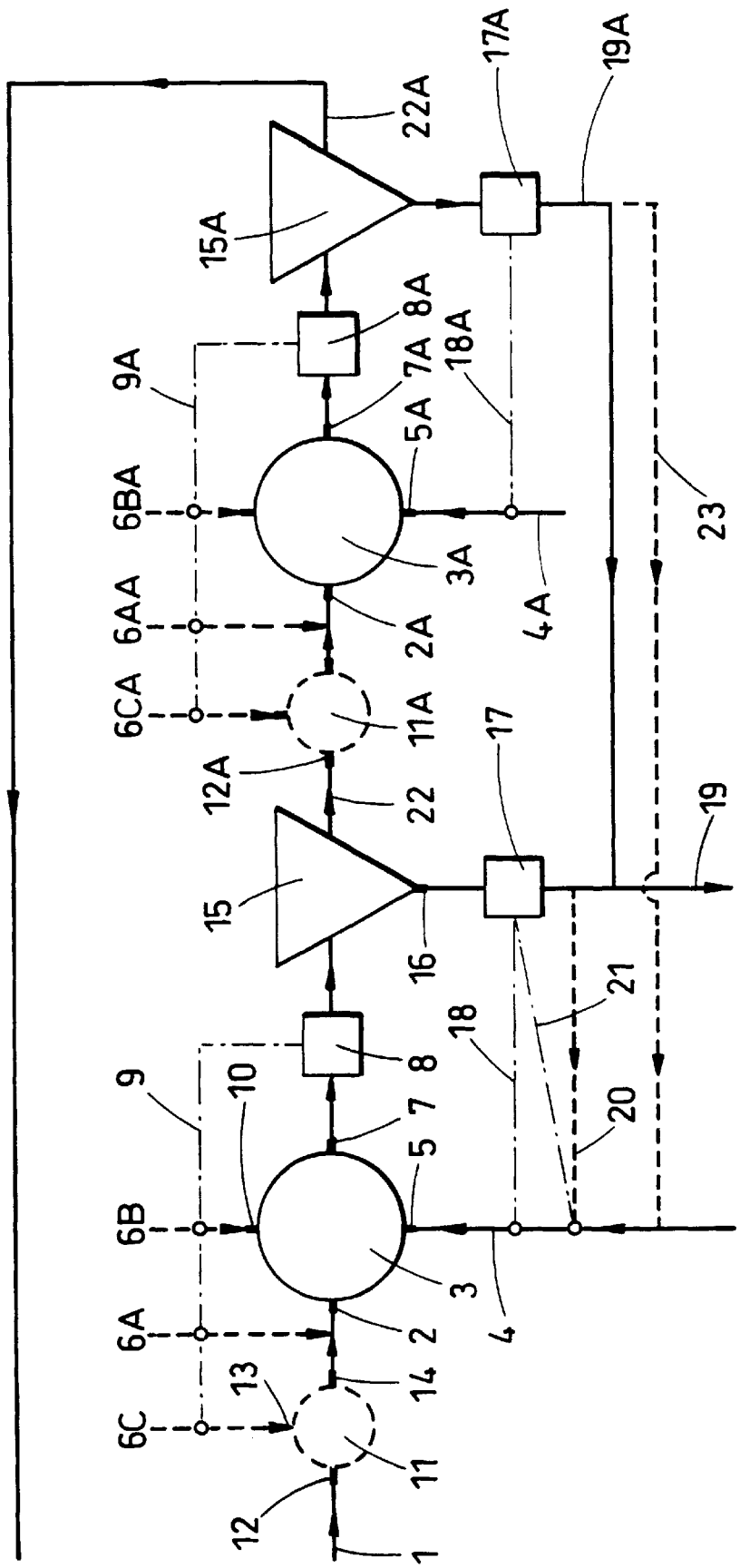

This invention relates to liquid-liquid extraction processes. In particular the invention relates to processes in which a first liquid phase containing a dissolved solute is contacted with a second liquid phase which is also a solvent for the solute but is immiscible with the first liquid phase, and the solute is extracted into the second liquid phase.

In some known extraction processes, an organic solute in weak solution in an organic solvent is contacted with an aqueous medium to extract the solute into the aqueous medium and thereby form a relatively concentrated aqueous solution in the aqueous medium. This procedure is called "back extraction" or "stripping". In some cases the solute is subjected to chemical treatment whilst in solution in the organic solvent to inter alia enhance the solubility of the solute in the aqueous medium, for example salt formation whilst in the organic solvent to enhance aqueous solubility of the solute as a salt.

In some processes the aqueous medium is in a circulating loop, in which a current of aqueous medium is allowed to contact a current of the solute dissolved in the organic solvent, thereby extracting a substantial proportion of the solute from the solvent, and then this aqueous medium containing extracted solute is circulated and allowed to contact fresh incoming solute dissolved in the organic solvent.

In one form of this circulating process, the aqueous medium is allowed to circulate several times so that the concentration of solute in the aqueous medium increases to an optimum. In some cases when the aqueous medium is in such a circulating loop, the organic solvent is itself in a circulating loop, for example resulting from a preliminary extraction into the organic solvent of the solute from an aqueous source of the solute, such as the product of a chemical reaction or fermentation, to pick up further solute and become more concentrated.

A general problem associated with such extraction processes, particularly when the aqueous medium is in a circulating loop, is that if only a limited degree of contact is achieved between the solute in the organic solvent and the aqueous medium, a relatively large volume ratio of aqueous medium:first organic solvent in the region of mixing is required. This can result in relatively bulky plant.

Moreover, some solutes are relatively unstable in both aqueous media and commonly used organic solvents, particularly if these are wet, and if only a limited degree of mixing is achieved between the solution in the organic solvent and the aqueous medium, particularly if the aqueous medium is circulated many times in the loop, the time for which the solute remains in the aqueous medium and the solvent is lengthened, to the detriment of the solute. This is particularly important in the case of pharmaceutical compounds, which are often sensitive to hydrolysis etc. in solution. Clavulanic acid is such a compound.

Clavulanic acid (Z)-(2R,5R)-3-(2-Hydroxyethylidene)-7-oxo-4-oxa-1-azabicyclo[3.2.0]heptane-2-carboxylic acid) is a β-lactamase inhibitor which is used commercially as a component of pharmaceutical formulations, usually in the form of its salts, especially potassium clavulanate. Clavulanic acid is produced commercially by culture of the microorganism *Streptomyces clavuligerus*, for example as described in GB 1508977.

Clavulanic acid or its salts may be extracted directly from the culture medium in various ways but normally the cells of the *S. clavuligerus* are first removed from the culture medium by such methods as filtration or centrifugation before such extraction procedures are commenced. Whole broth extraction may also be employed.

Clavulanic acid or its salts may be extracted from clarified culture medium by a variety of methods. Solvent extraction from cold clarified culture medium adjusted to acid pH values, and methods which utilize the anionic nature of clavulanic acid at neutral pH such as the use of anion exchange resins have been found to be particularly useful. A further useful method is to form an ester of clavulanic acid, purify the ester and regenerate the acid or its salt therefrom.

The extraction processes for obtaining clavulanic acid or its salts may notionally be divided into a primary isolation process followed by a further purification process.

Suitable primary isolation processes include solvent extraction of the free clavulanic acid. In the solvent extraction process the clavulanic acid is extracted into an organic solvent from cold clarified culture medium, which may be whole broth, adjusted to an acid pH value.

In one solvent extraction process for clavulanic free acid the clarified medium is chilled and the pH lowered into the region of pH 1–2 by the addition of acid while mixing with a substantially water-imiscible organic solvent. Suitable acids used to lower the pH include hydrochloric, sulphuric, nitric, phosphoric or the like mineral acids. Suitable organic solvents include n-butanol, ethyl acetate, n-butyl acetate and methyl isobutyl ketone, and other similar solvents. Methyl isobutyl ketone is a particularly suitable solvent for use in the extraction of the acidified culture filtrate. After separation of the phases clavulanic acid is found in solution in the organic phase.

The clavulanic acid may be back extracted from the organic phase into a new aqueous phase by making use of the greater water solubility of, for example, the alkali metal or alkaline earth metal salts of clavulanic acid in water than in organic solvents. Thus the clavulanic acid may be back extracted from the organic solvent into an aqueous solution or suspension of an alkali metal or alkaline earth metal base, such as sodium hydrogen carbonate, potassium hydrogen phosphate buffer or calcium carbonate, or water, while maintaining the pH at approximately neutrality, for example pH 7. This aqueous extract, after separation of the phases, may be concentrated under reduced pressure. Freeze-drying may also be employed to provide a solid crude preparation of the salt of clavulanic acid. Such solid preparations are stable when stored as a dry solid at −20° C. A similar process is described in GB 1563103. This process may be modified in known ways by for example additional purification steps applied to the organic solvent phase to remove high molecular weight impurities from the impure clavulanic acid.

A further secondary purification process for clavulanic acid is that described in for example EP 0026044, in which a solution of impure clavulanic acid in an organic solvent is contacted with t-butylamine to form the t-butylamine salt of clavulanic acid, which is then isolated, thereby separating the clavulanic acid from impurities remaining in the organic solvent, and the salt is then converted back to clavulanic acid or into a derivative of clavulanic acid such as an alkali metal salt or an ester. Other known secondary purification processes for clavulanic acid involve the use of other organic amines such as diethylamine, tri-(lower alkyl) amines, dimethylaniline and NN'-diisopropylethylenediamine to form salts and/or other derivatives thereof with the clavulanic acid. These purification process have the inherent disadvantage that they can introduce traces of the amine, or leave residual traces of salts of clavulanic acid with the amine, in the final product.

Such back extraction processes present a problem when clavulanic acid is prepared, as clavulanic acid is particularly water-sensitive. In conventional back extraction processes clavulanic acid can remain in contact with water for a long time, typically around an hour or more as the solution concentration of clavulanic acid builds up under the relatively gentle mixing and separating conditions generally used, and this can lead to extensive hydrolytic degradation.

The inventors have unexpectedly discovered that a known type of mixing device used in a novel way provides improved mixing conditions particularly suitable for such extraction processes.

Accordingly this invention provides an aqueous extraction process in which a stream of a substantially water imiscible organic solvent containing a water-soluble organic solute which is a beta-lactam antibiotic, such as a penicillin or cephalosporin, or clavulanic acid, as the free acid or a labile derivative or a salt thereof, is contacted at speed with a stream of an aqueous medium in a mixing region, so that a substantial proportion of the solute passes from the organic solvent into the aqueous medium in the first mixing region, then the organic solvent and aqueous phases are physically separated during a separation step, provided that if the solute is an amine salt of clavulanic acid which is formed in situ in the mixing region then the said amine salt is formed by reaction between clavulanic acid or a labile derivative thereof and an amine.

A preferred form of this invention provides a process for the isolation of an organic solute which is clavulanic acid in the form of the free acid, a salt thereof, particularly a salt with an amine, or other water-soluble derivative thereof from solution or suspension in a wholly or partly water-imiscible organic solvent in which the said solution or suspension is contacted in a mixing region which is a region of high turbulence and/or shear stress, with an aqueous medium, such that a solution of the said clavulanic acid in the form of the free acid, a salt thereof or other water-soluble derivative thereof in an aqueous phase is formed, then the organic solvent and aqueous phases are physically separated during a separation step, followed by a further processing step in which the clavulanic acid salt thereof or water-soluble derivative thereof is isolated from the aqueous solution.

The organic solvent should be substantially imiscible with the aqueous medium, such as an aliphatic ketone, for example methylisobutyl ketone. In the case of clavulanic acid, its salts and derivatives, suitable organic solvents include those described above, for example n-butanol, ethyl acetate, n-butyl acetate, and ketones of the general formula $R^1CO.R^2$ where $R^1$ and $R^2$ are independently $C_{1-10}$ alkyl groups, in particular methyl isobutyl ketone. The solution or suspension may contain impurities, for example high molecular weight impurities such as may be present if the solution has been obtained by a primary isolation process as described above, but preferably has been subjected to a preliminary purification process to remove at least some of the impurities. Suitable preliminary purification processes include filtration, and treatment with absorbent carbon. The solution may also contain small quantities of dissolved or suspended water, but preferably if the solution has been obtained from a primary isolation process it may be subjected to a dewatering process, for example centrifuging to remove droplets of suspended water.

Salts of these solutes may be of a metal ion such as sodium or potassium, or of an organic base such as an amine. When the organic solute is clavulanic acid it is preferred that the clavulanic acid is in the form of a salt with an amine.

Generally when a salt is present in the organic solvent phase it will be in the form of a suspension, as salts are usually insoluble in organic solvents. Such a suspension may comprise particles of the solid salt, or an emulsion of small droplets of a solution of the salt in water, which may form if the organic solvent itself is wet with dissolved or suspended water.

A suitable solution concentration for a solution or suspension of clavulanic acid, its salt or its derivative is around 500 to 20,000 $\mu$g/ml (0.0025M to 0.1M), for example around 1,000–5,000 $\mu$g/ml (i.e. 0.005M to 0.025M), typically around 3,000±1,000 $\mu$g/ml (i.e. 0.015 M±0.005 M) expressed in terms of clavulanic acid content. The process of the invention is suitable for higher solution contents of clavulanic acid, e.g. in line with improvements in fermentation culture yields.

Suitable salts of clavulanic acid for which the process of the present invention is suitable include salts of clavulanic acid with amines, for example with tertiary butylamine, the amines disclosed in WO93/25557, and in EP 0562583A, the contents of which are included herein by way of reference.

Generally suitable amines are covalent compounds of the general formula $R-NH_2$, where R is hydrogen (i.e. ammonia) or an organic group. Particular such amines include phenylethylamine, t-amylamine, t-octylamine, 1-hydroxy-2-methyl-2-propylamine, cyclopentylamine, cycloheptylamine, 1-adamantanamine, N-ethylpiperidine, N'N'-diisopropylethylenediamine and N N-dimethylcyclohexylamine.

Examples of other such amines include $C_1$–$C_{10}$ n- iso- and tert-alkylamines, dicyclohexylamine, adamantylamine, NN-diethylcyclohexylamine, N-isopropylcyclohexylamine, N-methylcyclohexylamine, cyclopropylamine, cyclobutylamine, norbornylamine, dehydroabietylamine, 1-hydroxy-2-methyl-2-propylamine, tri-n-propylamine, tri-n-octylamine, tri-n-butylamine, dimethylamine, i-propylamine, di-n-hexylamine, di-n-butylamine, diethylamine, 2-aminoethanol, NN-diethylethanolamine, NN-dimethylethanolamine, ethanolamine, n-butylamine, n-hexylamine, n-octadecylamine, N-ethylethanolamine, 1-hydroxyethylamine, diethanolamine, NN-dimethylethanolamine, N-ethyl diethanolamine, 1,6-diamino hexane, triethanolamine, diisobutylamine, diisopropylamine, 2-methoxyethylamine, hydroxylamine, ammonia, methylamine, ethylamine, n-propylamine, n-butylamine, n-pentylamine, n-hexylamine, n-heptylamine, n-octylamine, n-nonylamine, n-decylamine, n-undecylamine, n-dodecylamine, n-prop-2-ylamine, n-but-2-ylamine, n-pent-2-ylamine, n-hex-2-yl-amine, n-hept-2-ylamine, n-oct-2-ylamine, n-non-2-ylamine, n-dec-2-ylamine, n-undec-2-ylamine, n-dodec-2-ylamine, n-hex-3-ylamine, n-hept-3-ylamine, n-oct-3-ylamine, n-non-3-ylamine, n-dec-3-yl-amine, n-undec-3-ylamine, n-dodec-3-ylamine, n-oct-4-ylamine, n-non-4-ylamine, n-dec-4-ylamine, n-undec-4-ylamine, n-dodec-4-ylamine, n-non-5-ylamine, n-undec-5-ylamine, n-dodec-5-ylamine, and n-octadecylamine, 1-phenylethylamine, p-toluidine, p-aminobenzoic acid, p-bromoaniline, ethyl-4-aminobenzoate (ie benzocaine), benzylamine, diphenylamine, p-methyl-aminobenzene sulphonamide, m-nitroaniline, N,N'-dibenzylethylene-diamine (ie benzathine), diphenylmethylamine, 4-methylbenzylamine, 4-phenylbutylamine, N-ethyl piperidine, 2,6-dimethyl piperidine, 2-methyl-N-hydroxypropyl piperidine (i.e. cyclo-methycane), 4-methyl piperazine, 1-methyl-4-phenyl piperazine, N-ethyl morpholamine, hexamethylenimine, pyridine, 2-propylpyridine, 3-chloro-2-aminopyridine, morpholamine, 1,5-diazabicyclo[4,3,0]non-5-ene, 1,4-diazabicyclo[2,2,2]octane, pyrrolidone, quinuclidine, xanthinol, NN-diethylethylene diamine, NN'-diisopropylethylenediamine, triethylene tetramine, arginine, ornithine, histidine, lysine, benzylglycine, 3-amino-3-methylbutanoic acid, L-ethyl lysinate, L-methyl histidinate, methyl N-carbobenzyloxy-L-lysinate, methyl L-phenylalanate, ethyl glycyl glycinate, ethyl p-hydroxy phenyl glycinate, ethyl p-hydroxy phenyl glycinate, ethyl glycinate, ethyl L-tyrosinate, p-methoxybenzyl α-aminophenylacetate, n-butyl α-aminophenyl-acetate, methyl arginate, benzylglycine, benzyl phenylglycine, 1-nitrobenzyl phenyl glycine, n-butyl phenylglycine, p-methoxybenzyl phenylglycine, ethyl phenyl glycine, p-nitrobenzyl p-hydroxyphenylglycine, p-nitrobenzylserine, n-butyl serine, methyl arginine, dimethyl glutamate, p-nitrobenzyl tyrosinate, p-nitrobenzyl glycinate, benzylglycinate, p-nitrobenzyl α-amino-p-hydroxy-phenyl acetate, p-nitrobenzyl α-aminophenylacetate, ethyl α-amino-p-hydroxy phenyl acetate, ethyl L-tyrosinate.

In the case of clavulenic acid some of these salts with amines form solvates with some organic solvents, and/or hydrates, and processes which the salt is in such solvated and hydrated forms are encompassed within this invention.

The aqueous medium may for example be water or, as discussed further below, in two- or multi-stage processes of the invention may be a dilute solution of the solute.

The working conditions, e.g. concentrations of reactants, relative proportions of solutions used, flow rates, contact times etc., of the process are selected such that inter alia as much as possible of the clavulanic acid, its salt or derivative, is extracted from the solution in the organic solvent into the aqueous phase in a short time, and such that a concentrated solution of the clavulanic acid, its salt or derivative, in the aqueous phase is formed The contacting of the respective streams of organic solvent containing the solute and the aqueous medium may for example be carried out by merging the separate flow streams of the organic solvent phase and the aqueous medium phase in the mixing chamber of a mixing apparatus, the mixing chamber thereby comprising a contact region.

In the mixing region it is desirable to achieve as rapid and efficient contact between the components, i.e. organic solvent phase and aqueous medium phase as possible. It is desirable that in the mixing region any aqueous medium phase which is present as a separate phase is present in a form which has a high surface contact area with the organic phase, and for example the aqueous phase may be a dispersed emulsion phase, i.e. broken up into a form such as small droplets so as to create a high contact surface area between the two phases.

Efficient contact between the components may suitably be achieved using known mixing devices which provide a high degree of fluid turbulence and shear stress in the mixing region where liquids introduced into the mixing device mix, and which are capable of breaking up a separate water or aqueous phase into small droplets. Such mixers are known in the art, and selection of a suitable mixing device to achieve this will be apparent to those skilled in the art.

Suitable mixing devices include known in-line mixers, e.g. of the type in which one or more turbulence-creating elements are located within a pipeline during which the components are caused to flow. Another suitable type of mixer is a homogeniser, e.g. of the type in which two liquid phases are forced at pressure through a biased valve. Suitable mixing devices may also include cavities subjected to high turbulence and or shear stress by means of turbines, propellers etc.

Another and preferred type of mixer is a chamber wherein introduced fluids are subjected to intense rotational swirling, for example a vortex chamber of the type disclosed generally in EP-0153843-A (UK Atomic Energy Authority, the contents of which are incorporated herein by reference), the vortex chamber comprising a chamber of substantially circular cross section, e.g. generally cylindrical in shape, (alternatively the chamber may be substantially spherical, oblate spherical, ellipsoidal, conical, ogival etc.) and having at least one tangential inlet and an axial outlet. In such a mixer the components are fed in via the tangential inlet(s) and experience rotational swirling resulting in thorough mixing. The components may be fed in via a single tangential inlet if they are already in admixture before entry into the vortex chamber, or may each be fed in through a separate tangential inlet, to mix in the vortex chamber. The inner walls of the chamber may be smooth, or may alternatively be provided with inwardly projecting baffles or guides to direct fluid flow or to encourage mixing vortex formation or turbulence. The organic solvent phase and the aqueous medium phase may be each separately introduced through separate respective tangential inlets, or alternatively they may be introduced together through a single inlet.

The mixing procedure described above results in formation of an emulsion comprising fine droplets of the aqueous phase, for example comprising an aqueous solution of clavulanic acid, its salt or derivative, dispersed in a bulk phase of organic solvent. The aqueous and solvent phases are then physically separated in a separation step. Separation may be carried out using known separation devices, in particular centrifugal separators. A suitable type of centrifugal separator is a disc centrifuge. Such disc centrifuges generally consist of a chamber of generally circular internal section within which is a central disc stack, and a void space between the outer edge of the disc stack and the walls of the chamber. In view of the high ratio of organic phase to aqueous phase used in the process of this invention, as discussed above, it is desirable that the void space is relatively small. The construction and operation of such a centrifuge will be well known to those skilled in the art.

The emulsion may be fed from the mixing device directly to the separation device, preferably with as short a transfer time as possible so as to minimise hydrolytic degradation of the solute in the aqueous medium.

Alternatively, a mixer of the type described in EP-153843-A may be used, which comprises a vortex chamber as described above and having a combined separator stage which comprises a column forming an extension of the outlet and having, at or adjacent its end remote from the vortex chamber, spaced apart openings whereby fluids of different densities introduced into the chamber through the inlet(s) swirl through the chamber and the swirling flow from the chamber in passing along the column results in centrifugal separation of the fluids with the separated fluids emerging from the column through the spaced apart openings.

Using the components and mixing and separating devices as discussed above, the components may be fed into the mixing device and the emulsion of organic and aqueous phases which is formed in the mixing device may be fed into the separation device, the aqueous phase emerging as a separated phase from the separation device. The relative ratios of components fed into the mixing device will vary with conditions, principally the concentration of solute and solvent used in the organic solvent phase. In determining these ratios, as mentioned above it is preferred to monitor the concentration of the solute, e.g. clavulanic acid, its salt such as an amine salt, or derivative in the aqueous phase emerging from the separation device, and adjust the input of aqueous phase accordingly as determined by experiment to achieve and maintain the desired concentration. For example in the mixing region the volume ratio of aqueous medium:organic solvent phase may for example be in the range 1:50, e.g. 1:100, suitably 1:100–200.

Under the mixing conditions in the mixing region transfer of water-soluble solute from the organic solvent phase can take place relatively rapidly and efficiently. This helps to substantially reduce the time for which the solute resides in the aqueous medium and can thereby reduce the extent of hydrolysis of the solute.

The conditions of high turbulence and/or shear stress in the mixing/contact region enable the process of the invention to be carried out extremely rapidly, such that the time the aqueous phase need be in contact with the organic phase, and consequently the time a solute need remain in aqueous solution need be very short. The total time that the organic phase and aqueous phase are in contact may be less than one hour. Preferably the organic phase and aqueous phase are in contact for substantially less than this time, suitably 15 minutes or less, more preferably 10 minutes or less, more preferably 5 minutes or less, ideally as little a time as possible whilst also achieving a suitable degree of transfer of solute from the organic phase into the aqueous phase. Suitably the time the components of the process are in contact in the mixing region and the separation stage may be 0.5 to 3 minutes, for example the residence time of the organic phase in the contact region may be 0.5 to 2.0 minutes, e.g. 1 minute±15 seconds, and the residence time in the separation stage may suitably be 1.5 to 3.0 minutes, e.g. 2 minutes±15 seconds. In the case of clavulanic acid and its derivatives or salts this short residence time can be highly advantageous in reducing the extent of degradation of the clavulanic acid.

The time the components are in the mixing region and separation stage of the process can depend upon the scale of the process, but the general principles and specific process details set out in this disclosure provide guidance to those skilled in the art to set up a process suitable for industrial scale use.

During the course of the process of this invention, transfer of solute such as clavulanic acid, its salt or derivative, from the organic solution phase to the aqueous phase occurs. It is preferred that this transfer occurs as quickly as possible. Suitably more than 75%, preferably more than 80%, e.g. 90% or more of the solute transfers from the organic phase during the time the organic phase and the aqueous phase are in contact during the mixing and separation stages of the process. The extraction of this proportion of the solute, such as clavulanate ion, into the aqueous phase is a measurable property of the process, and can be used as a control parameter to control for example the input of the components.

The output of the separation step of the process is a concentrated aqueous solution of the solute, e.g. a salt of clavulanic acid, e.g. an amine salt of clavulanic acid such as with the amines discussed above, which may also contain dissolved organic solvent, and other impurities etc., together with a separate organic solvent phase output containing residual clavulanic acid in solution. This depleted solution of solvate in organic solvent may be subjected in a two or more stage process of this invention for a second and optionally subsequent time to the mixing and separation stages of the process of the present invention as described above, to extract a further proportion of the solute. Suitably in this way 90% or more of the total initial solute in solution in the organic solvent may be extracted into the aqueous phase, for example 93% or more, typically 96–98%. The extraction of this overall proportion of the solute is again a measurable property of the aqueous phase and may be used as a control parameter as outlined above.

The above-mentioned components may each be introduced separately into the mixing region, or alternatively they may be pre-mixed or blended upstream of the mixing region and then introduced into the contact region together.

In one form of this process the solute may be formed in situ in the organic solvent by having initially a solute precursor in the organic solvent, and treating this whilst in the organic solvent with a salt-forming compound. For example in the case of beta-lactam antibiotics the precursor may be the free acid of the antibiotic and a salt thereof such may be formed by admixing a salt forming compound such as an alkali metal alkoxide or an organic base, suitably an organic amine, with the precursor in the solvent. In the case of clavulanic acid the precursor may be free clavulanic acid and a salt thereof may be formed by admixing a salt forming compound such as an alkali metal alkoxide or, which is preferred, an amine such as those discussed above, with the precursor in the solvent. Such a solution of the precursor, e.g. the free acid, may be the product resulting from solvent extraction of an aqueous medium containing clavulanic acid, obtained as described above in a primary extraction process. Such a solution of the precursor, e.g. the free acid, may be fairly dilute, containing 1% by weight or less, e.g. 0.1–0.5% by weight of the free acid. The salt is then formed in the solvent, either as a solution of the salt in the solvent, or more usually as a heterogeneous suspension of particles of the salt or an emulsion of small droplets of a concentrated aqueous solution in the solvent if the salt is substantially insoluble in the solvent.

If the salt is formed in this way then the admixing of the salt-forming compound and the solution in the organic solvent may be carried out by introducing the salt forming compound into the (first) mixing region together with the organic solvent phase and the aqueous medium, or else the salt-forming compound and the organic solvent phase may be pre-mixed before introducing them into the mixing region with the aqueous medium.

The pre-mixing of the salt-forming compound and the organic solvent phase may itself be achieved by introducing the salt-forming compound such as an amine into a stream of the organic solvent phase, or may be achieved by introducing the salt-forming compound, and the organic solvent phase together into a second mixing region, i.e. a pre-mixing region. As with the first mixing region it is desirable that mixing occurs quickly, and therefore the second mixing region may be the mixing chamber of a second mixing apparatus, for example of one of the types of mixing apparatus discussed above, e.g. an in-line mixer or vortex chamber. This mixture formed by mixing the salt-forming compound and the organic solvent phase may then be introduced into the first mixing region as described above. Salt forming compounds such as the above-mentioned amines are generally soluble in organic solvents.

If the salt is formed in this way then the quantity of the salt-forming compound admixed with the organic solvent phase may be controlled by for example monitoring the pH of the mixture issuing from the first mixing region, and relating the quantity of salt-forming compound added to such a measurement, e.g. to ensure that all free acid is neutralized, or to indicate by alkalinity that excessive amounts of salt-forming compound such as amines are being used.

In the first mixing region the volume ratio of aqueous medium:organic solvent phase may for example be in the range 1:50 to 1:200, suitably 1:100–200. Under the mixing conditions in the first mixing region transfer of water-soluble solute from the organic solvent phase can take place relatively rapidly and efficiently. This helps to substantially reduce the time for which the solute resides in the aqueous medium and can thereby reduce the extent of hydrolysis of the solute.

After leaving the first mixing region the aqueous medium phase and the organic solvent phase are separated in a separation step as discussed above, generally on the basis of their imiscibility and/or difference in density. Separation may suitably be by mechanical separation, for example by standing in a separating tank until separation of two liquid phases occurs. Preferably mechanical separation is carried out more quickly by centrifuging, using for example a centrifugal separator as discussed above, or for example by introducing the mixed stream of aqueous medium phase and organic solvent phase into a fluidic contactor comprising a vortex stage and a separator stage such as described in EP 0153843A as discussed above.

The aqueous medium phase which is separated from the organic solvent phase may contain a high concentration of dissolved solute, for example 25–250 times the concentration of solvate or solvate precursor initially present in the organic solvent. The concentration of the solute in this aqueous medium phase may conveniently be measured by density, or by other conventional means. The concentration of solute in the aqueous medium phase is inter alia determined by the volume ratio of aqueous medium:organic solvent phase in the first mixing region, and by monitoring the density of the separated aqueous medium phase this volume ratio may be controlled. This separated aqueous medium phase may be subjected to further treatment etc. as discussed below.

Part of the aqueous medium phase which is separated from the organic solvent in this first separation stage may be fed into the flow of aqueous medium entering the first mixing region to produce an aqueous medium which is itself a dilute aqueous solution of the solute. By using a dilute aqueous solution of the solute as the aqueous medium in this first mixing region, and by controlling the concentration of solute in this dilute aqueous solution e.g. in response to fluctuations in the concentration of the aqueous medium which separates subsequent to the first mixing region, some compensation for fluctuations in the concentration of solute or solute precursor in the organic solvent may be made.

In the above aqueous extraction process a substantial proportion of the solute in the organic solvent phase may pass into the aqueous medium phase in the first mixing region, for example around 80% or more. The separated organic solvent phase may however contain a substantial residual quantity of the solute, because of the greater bulk of the organic solvent phase, even though the concentration of residual solute may only be around 0.05% by weight. It is consequently desirable to subject the organic solvent phase to a second separation stage.

Therefore in a preferred embodiment of the invention the separated organic solvent containing the residual solute is contacted at speed with further aqueous medium, in a third mixing region so that a further proportion of the solute passes into the aqueous medium, and the organic solvent phase and the aqueous medium phase are then subsequently separated. The aqueous medium may as above be water or a dilute aqueous solution of the solute.

In this preferred embodiment it is again desirable that mixing occurs quickly in the third mixing region may be the mixing chamber of a third mixing apparatus, which may be a mixing apparatus of one of the types discussed above, for example an in-line mixer or vortex chamber. It may be desirable to admix a further quantity of the salt-forming compound, which as previously may be introduced together with the organic solvent phase and the aqueous medium, or may be pre-mixed with the organic solvent phase as described above. Whether this further quantity of salt-forming compound is introduced or not, and the quantity introduced, may as above be determined and controlled by measurement of the pH of the separated aqueous medium phase.

Separation of the aqueous medium phase from the organic solvent phase after they leave the third mixing region may be by mechanical separation as described above.

In this second separation stage, the concentration of solute in the separated aqueous medium phase may be optimised at around the same concentration as that of the aqueous medium obtained in the first separation stage above. The concentration of this separated aqueous medium phase may as above be monitored by for example density and this monitoring can as above be used to control the amount of aqueous medium introduced into this third mixing region.

As the concentration of the solute in the organic solvent phase entering the third mixing region, having already been subjected to the aqueous extraction process in the first mixing region, is much more dilute than that in the solvent phase entering the first mixing region, to achieve a high aqueous medium concentration in this third mixing region a higher aqueous medium:organic solvent phase volume ratio of for example $1:\geq 250$, e.g. $1:\geq 750$, suitably around $1:\geq 500$ may be necessary. The aqueous medium:organic solvent phase volume ratios in the first and third mixing regions may be approximately proportioned to the respective solute concentrations in the organic solvent phases introduced respectively into the first and third mixing regions.

The separated aqueous medium phase from this separation stage subsequent to the third mixing region may be merged with the aqueous medium phase of similar concentrations from the separation stage subsequent to the first mixing region.

Alternatively, in the separation stage subsequent to the third mixing region the concentration of solute in the separated aqueous medium phase may be optimised at a lower concentration, for example of around 5% or less, to form an aqueous medium which is a dilute aqueous solution of the solute, and which may be circulated to form at least part of the aqueous medium introduced together with the organic solvent phase into the first mixing region. The concentration of solvate in the aqueous medium separated subsequent to the third mixing region may as above be monitored by for example density, and this monitoring may be used to control the volume ratio of aqueous medium:organic solvent phase in the third mixing region. Suitably if the aqueous medium from this separation stage is cycled back into the first mixing region as, or part of, a dilute aqueous solution of solute the volume ratio of aqueous medium:organic solvent phase in the third mixing region may be the same as that in the first mixing region.

The organic solvent separated subsequent to the third mixing region, and largely denuded of solute may be circulated to extract a fresh charge of solute, or a precursor thereof, from an aqueous source of the solute or precursor. Typically the source may be the product of a chemical or fermentation reaction in which a pharmaceutical compound is formed. The aqueous source may as a preliminary have been subjected to one or more essentially conventional purification procedures such as filtration, settling, flocculation etc., and/or physico-chemical treatments such as pH or temperature adjustment. The solution of the pharmaceutical compound in the organic solvent may also be subjected to further purification and or physico-chemical treatments, for example the above mentioned salt formation before introduction into the first mixing region as described above.

Prior to contacting this fresh source but subsequent to the third mixing region the organic solvent may be subjected to optional treatments for example essentially, conventional purification, or further physico-chemical treatments. For example if the solute has been subjected to chemical treatment whilst in the first solvent earlier in the circulation e.g. admixing of a salt-forming compound it may be desirable to apply a further chemical treatment prior to contacting fresh source to for example neutralize the effect of the earlier treatment, e.g. passage through a resin bed to extract impurities.

The extraction of fresh solute or precursor from an aqueous source by this circulated organic solvent may be achieved by bringing the solvent and the source into contact under mixing conditions. For example respective steams of the organic solvent and the source may be brought into contact in a fourth mixing region, so that a proportion, ideally a substantial proportion, of the solute or precursor in the source is extracted into the organic solvent, and subsequently separating the organic solvent and aqueous source phases. In this fourth mixing region it is again desirable that mixing occurs quickly, and the mixing region may be the mixing chamber of a fourth mixing apparatus of one of the types described above, for example an in-line mixer or a vortex chamber. Subsequent separation of the organic solvent phases and the aqueous source phase may be as described above with respect to the first mixing region and subsequent separation thereafter.

Regardless of whether the organic solvent is circulated in the above-described way or not, it may be desirable, prior to introducing the organic solvent containing the solute or solute precursor into the first mixing region, to apply essentially conventional purification procedures such as dewatering, filtration, purification to remove impurities etc.

The subsequent treatment of the aqueous medium following separation may be entirely conventional as understood in the art and may include purification steps, e.g. with charcoal, filtration etc.

For example if in the process of the invention clavulanic acid in the organic solvent is extracted as or converted in situ into an amine salt in aqueous solution, this amine salt may be subsequently be converted into a pharmaceutically acceptable salt or ester such as potassium clavulanate. In this conversion, recrystallisation of the amine salt of clavulanic acid or crystallisation by precipitation as a solvate such as the acetone solvate may be advantageous to further reduce the level of impurities. Such recrystallisation may be performed in a conventional manner, for example the salt in aqueous solution is treated with a large volume of solvating solvent such as acetone optionally with stirring and/or cooling to afford the crystallised product.

The salt of clavulanic acid with amine (II) optionally in the form of its solvate may be converted into clavulanic acid or a pharmaceutically acceptable salt or ester thereof by for example ion-replacement in the case of the free acid or salts, or by esterification.

Ion-replacement may be performed using ion-exchange resins, for example by passing a solution of the salt through a bed of a cation exchange resin in sodium, potassium or calcium form. Suitable cation exchange resins include Amberlite IR 120 and equivalent resins.

Alternatively ion-replacement may be effected by reaction of the protonated amine cation with a salt-precursor compound, which may be a base, for example a carbonate, bicarbonate or hydroxide of a pharmaceutically acceptable alkali or alkaline earth metal, or a salt of an organic carboxylic acid with a pharmaceutically acceptable cation such as an alkali or alkaline earth metal, for example a salt of an alkanoic acid of formula (IV):

$$R^{10}\text{—}CO_2H \tag{IV}$$

wherein $R^{10}$ is an alkyl group, containing for example from 1 to 20 carbon atoms, preferably from 1 to 8 carbon atoms. Examples of suitable salts include the acetate, propionate or ethylhexanoate salts, potassium 2-ethylhexanoate and sodium 2-ethylhexanoate being preferred. Typically the salt of clavulanic acid with an amine in solution may be reacted with a salt of an alkali metal with acid (IV) in solution or suspension in a suitable solvent, which may for example be an organic solvent, water, or a mixture of water and an organic solvent such as isopropanol. Suitably solutions of the salt of clavulanic acid with an amine and of the salt-precursor compound (IV) may be mixed, and the pharmaceutically acceptable salt allowed to crystallise. Suitably the reaction may be carried out of a temperature below ambient, e.g. 0 to 15° C., e.g. 0 to 10° C., suitably 0 to 0.5° C.

Suitable methods of esterification include:
a) the reaction of the salt of clavulanic acid with the amine (II) with a compound of the formula Q—$R^{11}$ wherein Q is a readily displaceable group and $R^{11}$ is an organic group;
b) the reaction of the salt of clavulanic acid with the amine (II) with an alcohol or thiol in the presence of a condensation promoting agent such as carbodiimide; and
c) the reaction of the salt of clavulanic acid with amine (II) with a diazo compound.

The foregoing processes extend to cover those aspects wherein the salt of clavulanic acid with amine (II) is first converted to clavulanic acid or another salt thereof and subsequently is converted to the desired ester. Further details of esterification methods are disclosed in GB 1508977 and 1508978. Use of the present invention enables salts and esters of clavulanic acid to be more readily obtained in pure form than operation of the processes of GB1508977 and 1543563.

In another aspect the present invention provides the use of a an in-line mixer, a homogeniser, a cavity subjected to high turbulence and or shear stress by means of turbines, propellers etc., or a vortex chamber of the type disclosed generally in EP-0153843-A (UK Atomic Energy Authority, the contents of which are incorporated herein by reference), the vortex chamber comprising a chamber of substantially circular cross section, e.g. generally cylindrical in shape, (alternatively the chamber may be substantially spherical, oblate spherical, ellipsoidal, conical, ogival etc.) and having at least one tangential inlet and an axial outlet, in a process to extract clavulanic acid as the free acid, a labile derivative or a salt, from an organic solvent phase into an aqueous medium phase, as a mixing region in which the organic phase and aqueous phases are mixed, provided that if the solute is an amine salt of clavulanic acid which is formed in situ in the mixing region then the said amine salt is formed by reaction between clavulanic acid or a labile derivative thereof and an amine.

The invention will now be described by way of example only with reference to:

FIG. 1: which shows an overall schematic diagram of a process of the invention.

FIG. 2: which shows a vortex chamber as used in the process of the invention.

Referring to FIG. 1, a process is shown schematically in which an aqueous extraction process of the invention is used. A stream of a solution of a solute precursor in a water-imiscible organic solvent, for example 0.25% by weight of a pharmaceutical compound, for example an acid such as clavulanic acid, is introduced along a flow line at (1). The stream is introduced via inlet (2) into a first mixing chamber (3). A stream of water in a flow line (4) is also introduced via inlet (5) into the first mixing chamber (3), the volume ratio water:solvent in the chamber (3) being around 1:100.

A salt-forming compound, such as an amine, e.g. a tertiary amine such as tertiary butylamine or one or more of the other amines discussed above, is also introduced into the system, via one of three alternative routes (6A), (6B) or (6C) as discussed below, and forms a water soluble salt solvate with the solute precursor. Under the mixing conditions in the mixing chamber (3) the salt solvate is extracted into the water phase to form an aqueous solution.

The mixed flow of organic solvent and aqueous solution emerges via outlet (7) of mixing chamber (3). The mixture is exposed to a pH meter (8), and the reading from this meter (8) is used as a control parameter in determining the amount of amine fed into the system via (6A), (6B) or (6C), by for example an electronic control (9) of the amine feed valves and meters—(not shown), so that if the aqueous phase is excessively alkaline, the amount of amine fed in is reduced, and vice versa.

The three alternative routes by which the amine can be fed in are as follows. Via (6A) the amine can simply be fed into the flow line (1) via a control valve etc. (not shown). Via (6B) the amine may be introduced via inlet (10) of first mixing (3). Via (6C) the flow line (1) and the flow of amine are introduced into a second mixing chamber (11) via inlets (12) (13) so that mixing occurs in the second mixing chamber (11), and the mixture issues from outlet (14) of second mixing chamber (11) before being introduced into first mixing chamber (3).

The mixed flow of aqueous solution and organic solvent emerging from outlet (7) of first mixing chamber (3) is passed into a separator (15), which is a centrifuge of conventional construction and operation but with a small void space, and which separates the aqueous solution and organic solvent phases. The aqueous solution issues from outlet (16) of the separator (15), and its density is measured using a density measuring instrument (17). The measurement of density is used as a parameter in the electronic control (18) of the input of water along flow line (4), the flow being adjusted to maintain an aqueous solution containing a desired concentration of solute.

The flow (19) of aqueous solution from the separator (15) may be subjected to further treatment, as conventional in the art, for example crystallisation, precipitation or further chemical treatment of the solute. Additional a bleed (20) of aqueous solution may be introduced into the stream of water in flow line (4) so that extraction of solute from the organic solvent by a dilute aqueous solution occurs. The quantity of aqueous solution bled into flow line (4) in this way may also be controlled (21) by relation to the density of the output from (16).

The flow of organic solvent phase (22) from separator (15) is depleted in solute but the quantity of residual solute is such that it is worth a second extraction with an aqueous medium to extract a second batch of solute. The organic solvent phase is therefore introduced into a third mixing chamber (3A) together with a flow of water (4A), and the mixed output stream and subjected to a second cycle of mixing and separation, in a manner analogous to that described above, corresponding parts having corresponding functions and being numbered correspondingly.

In this second cycle of mixing and separation various aspects differ from the first cycle. The addition of salt-forming compound such as an amine is optional, as sufficient may remain from the first cycle to combine with all the solute precursor. The flow of water or dilute aqueous solution of solute introduced into third mixing chamber (3A) may be adjusted to provide two alternative output solutions (19A). It may be adjusted to produce a solution of solute of similar concentration to the output (19) and which may be mixed with the output (19). For this first alternative the volume ratio of aqueous phase to organic solvent phase in the third mixing chamber (3A) may be much lower than in the first mixing chamber (3), typically around 1:500. It may alternatively be adjusted to produce a dilute aqueous solution of the solute, e.g. around 5% weight, which may be fed back via (23) into the input flow line (4) of the first mixing chamber (3). In this second alternative it is desirable that the volume ratio of aqueous phase:organic solvent phase in the third mixing chamber (3A) is approximately the same as that in first mixing chamber (3).

The flow of organic solvent (22A) from the output of the separator (15A) may be recycled and purified (not shown) and may be used to extract a further quantity of solute or solute precursor from an aqueous source of the same (not shown).

It will be understood by those skilled in the art that in the process scheme shown in Fig. there will be various meters, control systems, valves, pumps, surge tanks, monitors, control systems etc. standard in the art to operate the system at optimum efficiency. These are not shown for simplicity.

The mixing chambers (3), (3A), (11), (11A) may be mixing chambers of essentially conventional mixing apparatus of generally known type, for example in-line mixers. Alternatively these mixing chambers may be vortex chambers having one or more tangential inlets and an axial outlet of the type illustrated generally in FIG. 2.

Figure 2A:
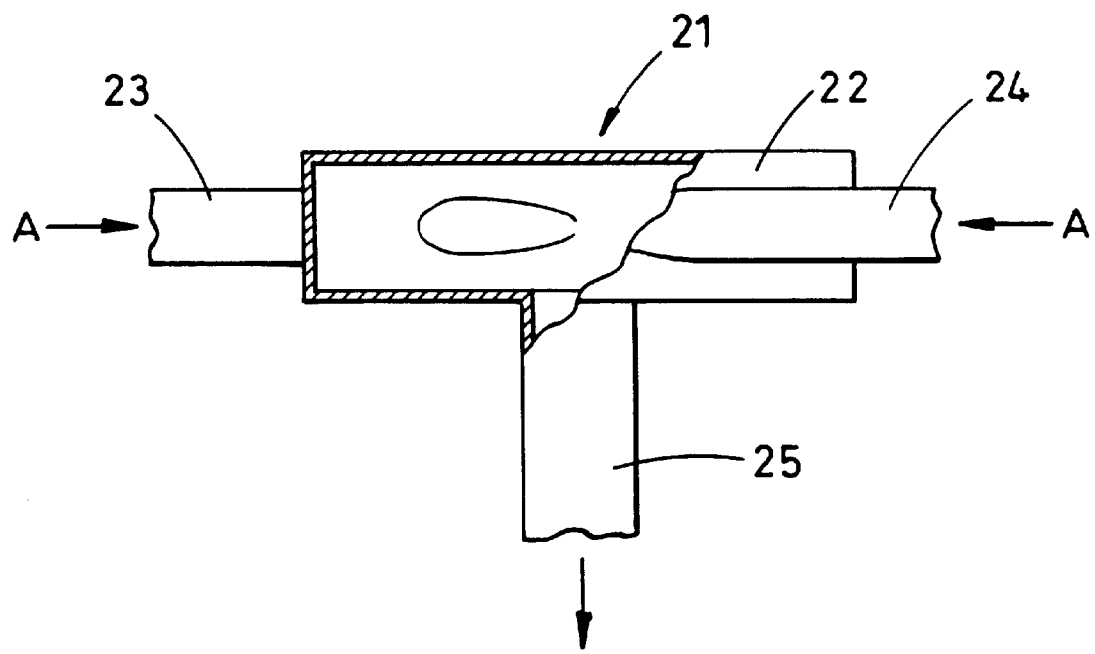
Figure 2B:
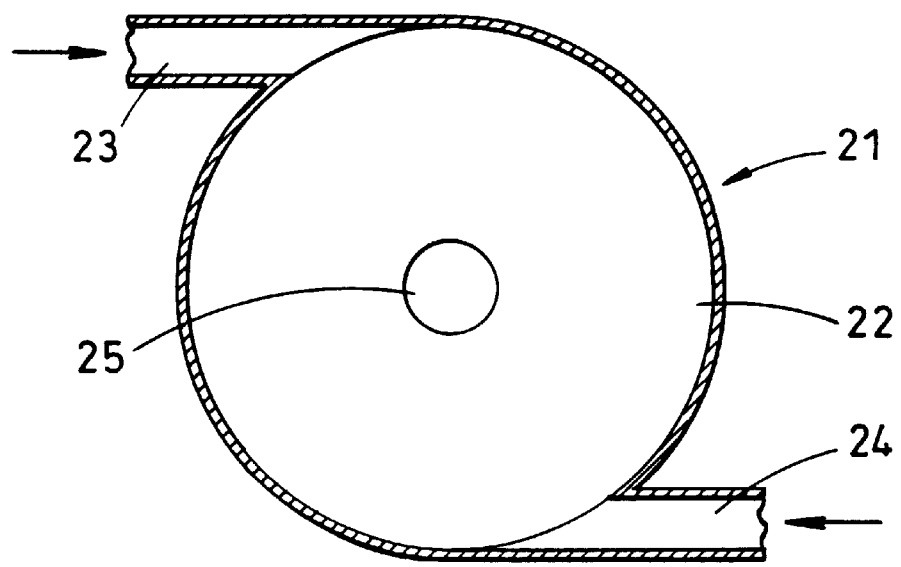

Referring to FIG. 2, a vortex chamber, shown overall (21), consisting of an essentially cylindrical chamber (22), having respective first and second tangential inlets (23) (24) and a single axial outlet (25) is shown in a part-sectional side-on view in FIG. 2A, and in a sectional plan view through the plane A—A of FIG. 2A, in FIG. 2B. In operation first and second liquids (not shown) are introduced at speed through the respective first and second tangential inlets (23),(24) in the direction of the arrows shown and a vortex is formed within the chamber (22) in which the first and second liquids mix. The flow of mixed first and second liquids leaves the chamber (22) via the axial outlet (25). The mixing chambers (3), (3A), (11) and (11A) may be such vortex chambers.

It will be appreciated by those skilled in the art that the schematic diagram of FIG. 1 is simplified to omit specific detail of valves, pumps, surge tanks, pipework etc. conventional in the art of chemical engineering. The construction of a processing system along the lines of that illustrated in FIG. 1 will be within the normal abilities of a chemical engineer skilled in the art.

I claim:

1. An aqueous extraction process comprising the steps of:
   a) contacting at speed a stream of substantially water imiscible organic solvent containing a water-soluble organic solute which is a beta-lactam antibiotic selected from a penicillin, cephalosporin and clavulanic acid, as the free acid or a labile derivative or a salt thereof, with a stream of an aqueous medium in a first mixing region, such that a substantial portion of the solute passes from the organic solvent into the aqueous medium in the first mixing region; and b) physically separating the organic solvent and aqueous phases during a separation step;

provided that if the solute is an amine salt of clavulanic acid which is formed in situ in the first mixing region then the amine salt is formed by reaction between clavulanic acid or a labile derivative thereof and an amine.

2. A process according to claim 1, for the isolation of an organic solute which is clavulanic acid in the form of a salt with an amine from a solution or a suspension in a wholly or partly water imiscible organic solvent in which the solution or the suspension and an aqueous medium are introduced at speed into a first mixing region which is a region of high turbulence and/or shear stress, such that a solution of the clavulanic acid salt in an aqueous phase is formed, then the organic solvent and aqueous phases are physically separated during the separation step, followed by a further processing step in which the clavulanic acid salt is isolated from the aqueous solution.

3. A process according to claim 1 characterised in that the organic solvent is an aliphatic ketone.

4. A process according to claim 1 characterised in that the solute is in the form of a salt of a metal ion or of an organic base.

5. A process according to claim 4 characterised in that the organic solute is clavulanic acid in the form of a salt with an amine.

6. A process according to claim 2 or 5 characterised in that the amine is selected from tertiary butylamine, ammonia, phenylethylamine, t-amylamine, t-octylamine, 1-hydroxy-2-methyl-2-propylamine, cyclopentylamine, cycloheptylamine, 1-adamantanamine, N-ethylpiperidine, N,N'-diisopropylethylenediamine and N,N-dimethylcyclohexylamine.

7. A process according to claim 1 characterised in that the mixing region comprises a mixing device which provides a high degree of fluid turbulence and shear stress in the mixing region where liquids are introduced into the mixing device mix, and which is capable of breaking up a separate water or aqueous phase into small droplets.

8. A process according to claim 7 characterised in that the mixing device is selected from in-line mixers of the type in which one or more turbulence-creating elements are located within a pipeline during which the components are caused to flow, homogenisers of the type in which two liquid phases are forced at pressure through a biased valve, cavities subjected to high turbulence and or shear stress by means of turbines or propellers.

9. A process according to claim 7 characterised in that the mixing device comprises a vortex chamber of substantially circular cross section, and having at least one tangential inlet and an axial outlet, and the respective streams of organic solvent containing the solute and the aqueous medium are introduced via the said at least one tangential inlet.

10. A process according to claim 7 characterised in that the aqueous and solvent phases are then physically separated in a separation step using a centrifugal separator.

11. A process according to claim 1 characterised in that in the mixing region the volume ratio of aqueous medium:organic solvent phase is in the range of 1:200 to 1:50.

12. A process according to claim 1 characterised in that the total time that the organic phase and aqueous phase are in contact is less than one hour.

13. A process according to claim 12 characterised in that the organic phase and aqueous phase are in contact for 15 minutes or less.

14. A process according to claim 12 characterised in that the organic phase and aqueous phase are in contact in the contact region and the separation stage is 0.5 to 3 minutes.

15. A process according to claim 1 characterised in that the organic solvent phase output from the separation step of the process, containing residual clavulanic acid in solution is subjected in a two or more stage process for a second and optionally subsequent time to the mixing and separation steps, to extract a further proportion of the solute.

16. A process according to claim 1 characterised in that the solute is formed in situ in the organic solvent by having initially a solute precursor in the organic solvent, and treating this whilst in the organic solvent with a salt-forming compound.

17. A process according to claim 16 characterised in that the solute precursor is clavulanic acid and the salt forming compound is an amine.

18. A process according to claim 1 characterised in that part of the aqueous medium phase which is separated from the organic solvent in the separation stage is fed into the flow of aqueous medium entering the mixing region to produce an aqueous medium which is itself a dilute aqueous solution of the solute.

19. A process according to claim 1 characterised in that the separated organic solvent phase is subjected to a second separation phase.

20. A process according to claim 19 characterised in that the separated organic solvent containing the residual solute is contacted at speed with further aqueous medium, in a further mixing region so that a further proportion of the solute passes into the aqueous medium, and the organic solvent phase and the aqueous medium phase are then subsequently separated.

21. A process according to claim 20 characterised in that in the further mixing region an aqueous medium:organic solvent phase volume ratio of $1:\geqq 250$ is used.

22. A process according to claim 19 characterised in that the separated aqueous medium phase from the further separation stage subsequent to the further mixing region is merged with the aqueous medium phase of similar concentrations from the separation stage subsequent to the first mixing region.

23. A process according to claim 19 characterised in that in the separation stage subsequent to the further mixing region the concentration of solute in the separated aqueous medium phase is optimised at a low concentration to form an aqueous medium which is a dilute aqueous solution of the solute, and which is circulated to form at least part of the aqueous medium introduced together with the organic solvent phase into the first mixing region.

24. A process according to claim 19 characterised in that the organic solvent separated subsequent to the further mixing region is circulated to extract a fresh charge of solute, or a precursor thereof, from an aqueous source of the solute or precursor.

25. A process according to claim 1 characterised in that clavulanic acid in the organic solvent is extracted as or converted in situ into an amine salt in aqueous solution, which is subsequently converted into a pharmaceutically acceptable salt.

26. A process according to claim 25 characterised in that the pharmaceutically acceptable salt of clavulanic acid is potassium clavulanate.

27. A process according to claim 20 characterised in that the further mixing region comprises a vortex chamber of substantially circular cross section and having at least one tangential inlet and an axial outlet, and the respective separated organic solvent containing the residual solute and further aqueous medium are introduced through at least one tangential inlet.

* * * * *